United States Patent [19]
Latulippe

[11] Patent Number: 5,518,115
[45] Date of Patent: May 21, 1996

[54] STERILIZATION AND STORAGE CONTAINER TRAY INCLUDING GROMMETS

[75] Inventor: Michael L. Latulippe, Derry, N.H.

[73] Assignee: Poly Vac Incorporated, Manchester, N.H.

[21] Appl. No.: 310,567

[22] Filed: Sep. 22, 1994

[51] Int. Cl.$^6$ ............................... B65D 51/16; A61L 2/26
[52] U.S. Cl. .................. 206/370; 206/438; 211/60.1; 211/70.6; 220/315; 422/300; 422/310
[58] Field of Search ........................ 206/370, 438, 206/439; 422/297, 300, 310; 211/70.6, 60.1; 220/315, 318, 324

[56]  References Cited

U.S. PATENT DOCUMENTS

| 1,618,027 | 2/1927 | Vogler | 211/60.1 X |
| 3,431,041 | 3/1969 | Fontlladosa | 211/60.1 X |
| 3,604,565 | 9/1971 | Freeman | 211/70.6 |
| 3,743,088 | 7/1973 | Henkin | 206/438 X |
| 3,759,538 | 9/1973 | Fabiano | 211/70.6 X |
| 4,117,937 | 10/1978 | Ratti | 211/70.6 |
| 4,229,420 | 10/1980 | Smith et al. | |
| 4,512,498 | 4/1985 | Leibinger | 422/300 X |
| 4,544,351 | 10/1985 | Marsicano | |
| 4,643,303 | 2/1987 | Arp et al. | |
| 4,643,674 | 2/1987 | Zdarsky | |
| 4,728,504 | 3/1988 | Nichols | |
| 4,783,321 | 11/1988 | Spence | |
| 4,798,292 | 1/1989 | Hauze | |
| 4,915,913 | 4/1990 | Williams et al. | 422/310 X |
| 5,046,624 | 9/1991 | Murphy et al. | |
| 5,048,700 | 9/1991 | Feder | 211/70.6 |
| 5,098,676 | 3/1992 | Brooks, Jr. | |

FOREIGN PATENT DOCUMENTS

| 1364546 | 1/1988 | U.S.S.R. | 220/315 |
| 2198119 | 6/1988 | United Kingdom | 220/315 |

Primary Examiner—Bryon P. Gehman
Attorney, Agent, or Firm—Hayes, Soloway, Hennessey, Grossman & Hage

[57]  ABSTRACT

A sterilization tray assembly for sterilizing, transporting and storing surgical instruments, having top and bottom mating enclosures. The mating enclosures each have a plurality of ports for permitting ingress and egress of gaseous sterilant. A rack dimensioned to fit within the bottom enclosure is fitted within the enclosure. The rack has a plurality of spaced apertures into which are mounted grommets formed of an elastomeric material having an inside diameter dimensioned to receive a selected surgical instrument therein.

6 Claims, 5 Drawing Sheets

STERILIZATION AND STORAGE CONTAINER TRAY INCLUDING GROMMETS

FIELD OF THE INVENTION

This invention relates to sterile container systems generally, and more particularly to container systems for the sterilization and subsequent sterile storage of medical surgical instruments and the like.

BACKGROUND OF THE INVENTION

Surgical procedures are regularly performed using "sets" of pre-selected surgical instruments, each set being a collection of instruments established from experience to be useful in a given surgical procedure. For example, the surgical instruments expected to be used in an obstetrical procedure are grouped together to form a set and, as a set, are sterilized, stored on a pan or tray, and finally transported on that tray to the operating room when their use is required.

Sterilization of reusable and delicate, precision surgical instruments and their subsequent sterile storage is of paramount concern to surgeons and hospitals. Sterilized surgical instruments are essential during surgical procedures to minimize coming in contact with a suitable medium, may incubate to harmful levels. Condensation remaining after sterilization, either in the tray or on the instruments, provides such a medium for the growth of deleterious bacteria during the subsequent storage of the sterilized instruments.

Some example prior art patents which provide for sterilization containers are Arp et al, U.S. Pat. No. 4,643,303, Nichols, U.S. Pat. No. 4,728,504, and Spence, U.S. Pat. No. 4,783,321. These prior art patents generally teach the use of baskets or trays to hold the instruments to be sterilized, and apertures in the baskets which allow for gross drainage of condensation from the baskets to the container floor below the basket. The condensation then must again drain from the container floor. This double drainage increases the risk of condensation remaining in proximity to the sterilized instruments and the subsequent contamination of the condensation by airborne bacteria. These prior art baskets or instrument retention devices are of such design that excessive condensation may be trapped between the instruments and the device.

Many prior art patents have no separate container locking device to provide a sealing effect between the container halves. Thus, the flow of steam or other gaseous sterilants during the sterilization is not firmly restricted to the apertures. More sterilization, thus increasing the risk of airborne bacterial contamination of any remaining condensation.

U.S. Pat. No. 4,643,303 describes a sterilization container enclosing an instrument basket within a box-like base and cover. The container also includes clamps mounted to the container by hinges for releasably holding the cover to the base, U.S. Pat. No. 4,783,321 describes a sterilization container enclosing an instrument basket within a base and cover. The container also includes a latch mechanism for releasably holding the cover to the base.

Most of the prior art, for example, Nichols U.S. Pat. No. 4,728,504, provide for the placement of the instruments on a removable basket or tray which includes apertures formed on the bottom of the tray to allow for the drainage of condensation. The domed configuration of the tray bottom in U.S. Pat. No. 4,728,504 allows for sufficient surface area contact with the instruments such that condensate may be held between the instruments and the tray after sterilization. Such a risk of airborne bacterial contamination of remaining condensation after sterilization increases during increased storage of the sterilized instruments. Thus, it is imperative to remove as much condensation as possible from the container and from the instruments after sterilization.

Hauze, U.S. Pat. No. 4,798,292, describes a non-locking sterilization container with apertures arranged in rows and columns enclosing a flat surfaced insert with apertures arranged in rows and columns such that the apertures in the container and the insert are vertically aligned. Pegs are inserted in the insert apertures to provide horizontal separation of the instruments during sterilization and subsequent presentation of the instruments. The flat surface of the insert and the pegs increase the risk of condensation remaining in proximity to the instruments after sterilization.

The foregoing discussion of the prior art was taken from Brooks, U.S. Pat. No. 5,098,676 which describes an improved sterilization tray assembly for sterilizing, transporting and storing instruments, which overcomes the aforesaid and other disadvantages of the prior art. Brooks provides a sterilization tray assembly comprising an upper tray section including a plurality of upper tray ports spaced in a predetermined pattern; a lower tray section including a plurality of lower tray ports spaced in a predetermined pattern; and locking means for engaging the upper tray section and the lower tray section to form a sealing contact between the upper and lower tray sections. A mat made of silicone rubber and sized to fit the tray is positioned between the tray sections. The mat has an upper surface and a lower surface, and includes a plurality of ports in the mat spaced in a predetermined pattern wherein the mat ports and the lower tray ports are in vertical alignment. The mat also has a plurality of upwardly tapered, vertical projections spaced in a predetermined pattern on the upper surface, the vertical projections having tips at their free ends to provide support for instruments above the upper surface; and a plurality of downwardly projecting support feet depending from the lower surface spaced in a predetermined pattern for spacing the lower surface above the lower tray section.

The sterilization tray assembly as described in U.S. Pat. No. 5,098,676 is available commercially from PolyVac, Inc. of Manchester, N.H., and has achieved substantial commercial success. However, the spring locking hinges as described in U.S. Pat. No. 5,098,676 may not always be adequate, particularly in the case of large sterilization trays which may become quite heavy when loaded. Also, while the silicone rubber mat as described in U.S. Pat. No. 5,098,676 provides a convenient support for larger surgical instruments; smaller instruments may not be securely held. Accordingly, PolyVac, Inc. and others have introduced sterilization trays including one or more holding strips specifically designed to releasably hold selected surgical instruments.

The present invention is an improvement over the sterilization, transporting and storage container trays such as described in U.S. Pat. No. 5,098,676.

SUMMARY OF THE INVENTION

In one aspect, the present invention provides a sterilization, transporting and storage container tray assembly for a surgical instrument kit. The tray assembly includes top and bottom locking trays enclosing a rack assembly mounted in the bottom tray. The rack includes a plurality of spaced apertures which are preferably equi-sized, in which are mounted grommets having selected inside diameter's for releasably gripping selected surgical instruments. The grommets are formed of an elastomeric material such as silicone rubber that maintains its resiliency over repeated temperature cycling, e.g. for sterilization. Ports are provided in the top and bottom trays for permitting ingress and egress of steam or other gaseous sterilants. The rack is separated from the interior walls of the bottom tray by spacers or projections so as to permit free flow of steam and other gaseous sterilant within the package, and to facilitate condensation drainage. If desired, but not necessarily, indicia are printed on the rack and/or the inside surface of the top tray, identifying instruments for a pre-defined surgical procedure.

Completing the sterilization, transporting and storage tray assembly are at least one pair of locking hinges or clips for locking the top and bottom trays together. The locking hinges or clips may comprise spring metal clips for example, as shown in FIG. 8 of the aforesaid U.S. Pat. No. 5,098,676. In a preferred embodiment of the invention, at least one of the pairs of the clamps comprise generally C-shaped clamps pivotally mounted to a lever arm which in turn is pivotally mounted to the top tray.

BRIEF DESCRIPTION OF THE DRAWINGS

The foregoing and other objects of the present invention and various features and details of the operation and construction thereof are hereinafter more fully set forth with reference to the accompanying drawings, wherein like numerals depict like parts, and wherein.

DETAILED DESCRIPTION OF THE PREFERRED EMBODIMENT

Figure 1:
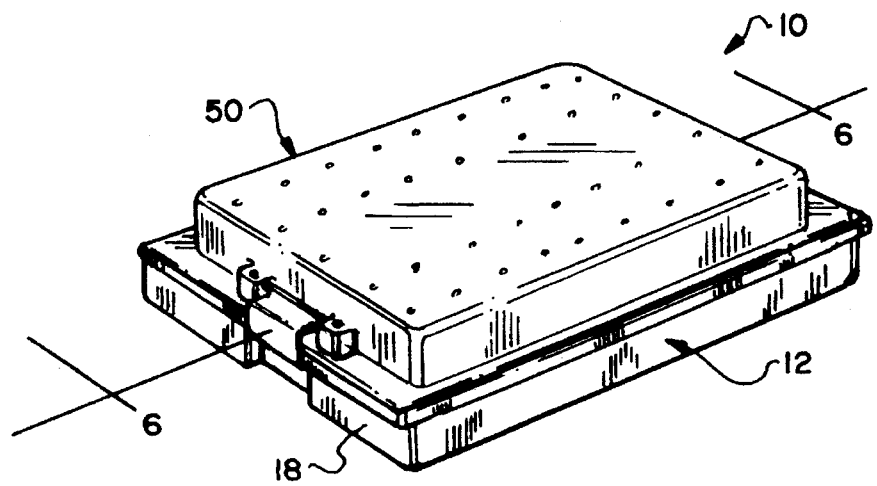
FIG. 1 is a perspective view of the preferred embodiment of the invention showing the tray assembly in the closed and locked position.

Referring now to the drawings, and in particular to FIGS. 1–6, the sterilization, transporting and storage tray assembly of the present invention is indicated generally by numeral 10. The tray assembly 10 consists of a box-like bottom tray 12 having a bottom 14 and four generally perpendicular upwardly projecting continuous sidewalls comprising a front sidewall 16, a left sidewall 18, a back sidewall 20 and a right sidewall 22. Tray bottom 14 includes a plurality of spaced apertures 24 arranged in a predetermined pattern. Apertures 24 permit ingress and egress of steam or other gaseous sterilants, and allow for condensation drainage.

An instrument support tray 30 having a generally planar top surface 32 and a downwardly projecting lip 34 which forms the periphery of tray 30, is inserted in, and rests within base 12. Tray 30 is mounted within base 12 spaced from the base side walls 16, 18, 20 and 22, for example, by a pair of raised tabs or detents 36 which cooperate with appropriately located apertures 38 in the base side walls 16 and 18 whereby to form a gap between the periphery of lip 34 and the inside of walls 16, 18, 20 and 22. Gap 40 permits ingress and egress of steam or other gaseous sterilants and allows for condensation drainage. Distribution of steam or other gaseous sterilants within the interior of the assembly and condensation drainage may be enhanced by an apertured riser 41 which communicates with apertures 39 in tray 30 (See FIG. 3).

A feature and advantage of the present invention is to provide a surgical instrument delivery system for pre-defined surgical procedures in which a selection of tools with a range of sizes and styles may be prepackaged for use in a logical sequence of operations. For example, as applied to dental implant surgery, a typical sequence of steps may comprise first drilling a pilot hole, for example, in the jaw bone, the pilot hole is then enlarged and then threaded using a thread former. Threaded pins are then mounted in the threaded holes using a driver. As will be appreciated these various tools comprise different diameters. While the holes for accommodating the instruments may be custom drilled, i.e. to accommodate instruments of different diameters, in a preferred embodiment of this invention, in order to facilitate manufacture of the tray, a plurality of equi-sized holes 42, are drilled in the tray in a predetermined layout, and grommets for releasably gripping selected surgical instruments such as drill bits, drivers, etc. are mounted in the holes. Grommets 44 which are formed of an elastomeric material that maintains its resiliency over repeated temperature cycling, for example, silicone rubber or the like, have different sized apertures 46a, 46b, 46c (FIG. 8) to accommodate different sized instruments. The layout of holes 42 in tray 30 and the mounting of particular sized grommets will depend on the particular tool to be mounted at that particular position in the tray.

Figure 5:
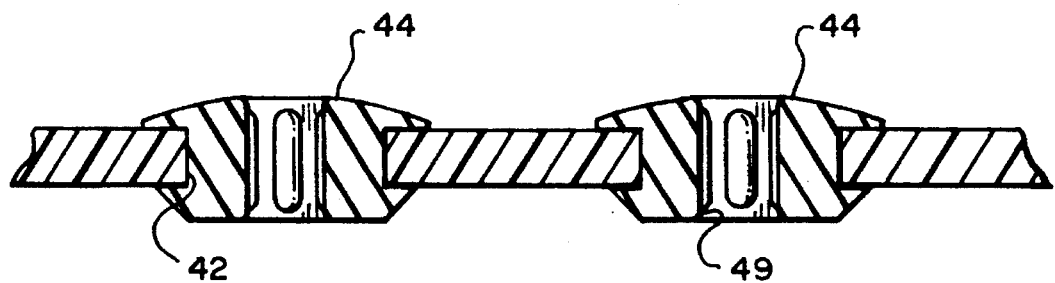
FIG. 5 is a partial sectional view taken along line 5—5 of FIG. 4.
Figure 8:
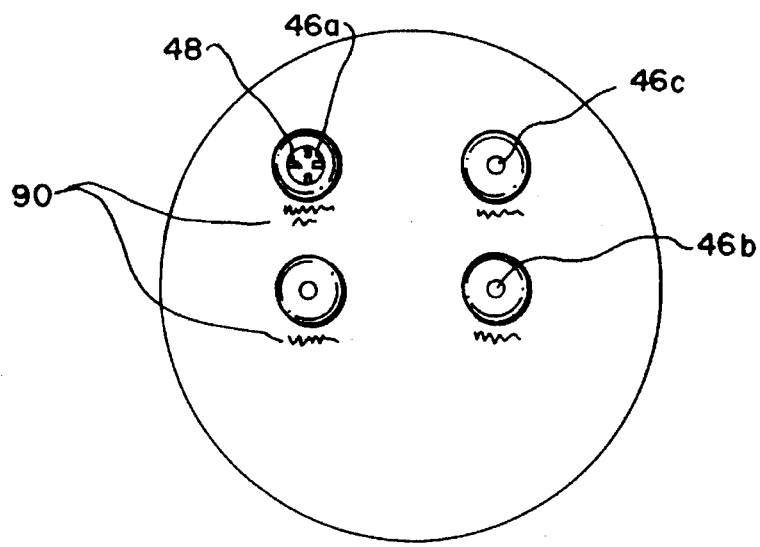
FIG. 8 is an enlarged top plan view of the portion designated "FIG. 7" in FIG. 4.

Referring in particular to FIGS. 5 and 8, a plurality of inwardly extending projections or ribs 48 are integrally formed on the inside wall surfaces 49 of the grommet apertures. As shown in FIG. 8, ribs 48 are equi-spaced around the periphery apertures 46. While four ribs 48 are shown in FIG. 8, as few as three ribs, or five or more ribs may be provided.

Preferably, but not necessarily, indicia 90 are printed adjacent the various grommets identifying the individual tools; and, if desired, duplicate tools are arranged adjacent one another on the tray.

Figure 9:
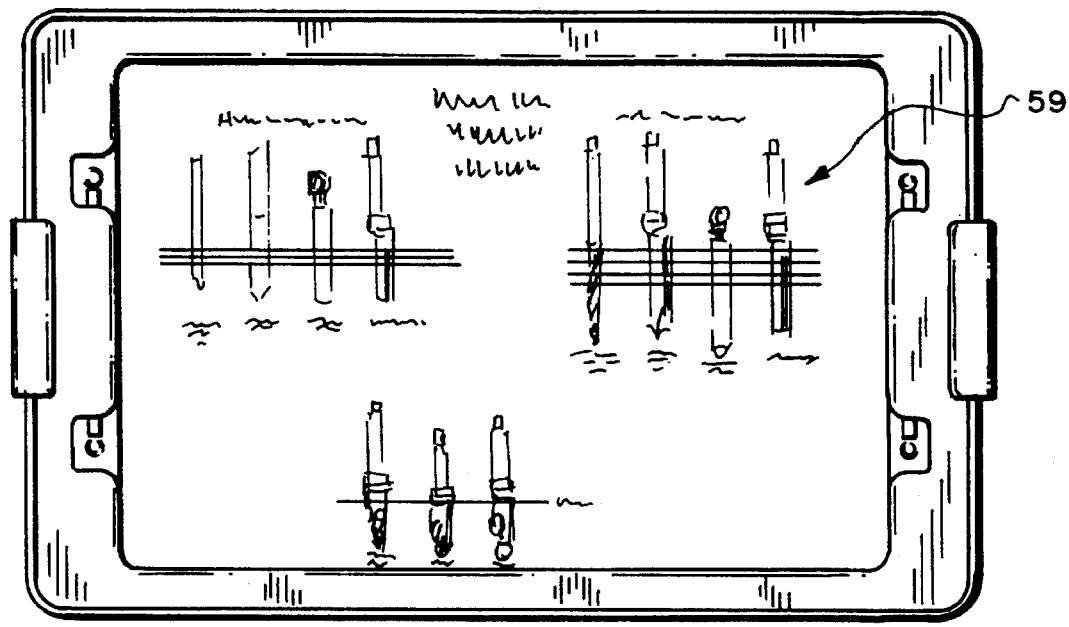
FIG. 9 is a plan view showing the underside of the top tray.

Top 50 is of a box-like shape and includes a top surface 52 having a plurality of spaced apertures 54 arranged around the periphery of the top surface 52 to permit the ingress and egress of steam or other gaseous sterilants during sterilization, and drainage of condensation from the top surface 52. Top 50 includes an outwardly projecting peripheral ridge section 56, and a downwardly projecting lip section 58 which together engage the top portions of walls 16, 18, 20 and 22 of base 12 when the top 50 is locked upon the base 12. This sealing contact causes the steam of other gaseous sterilants to ingress and egress the container tray 10 only through apertures 24 and 54. If desired, an instrument key, such as a drill depth guide or the like, may be printed on the inside surface 59 of the top cover 50, e.g. as shown in FIG. 9.

Figure 2:
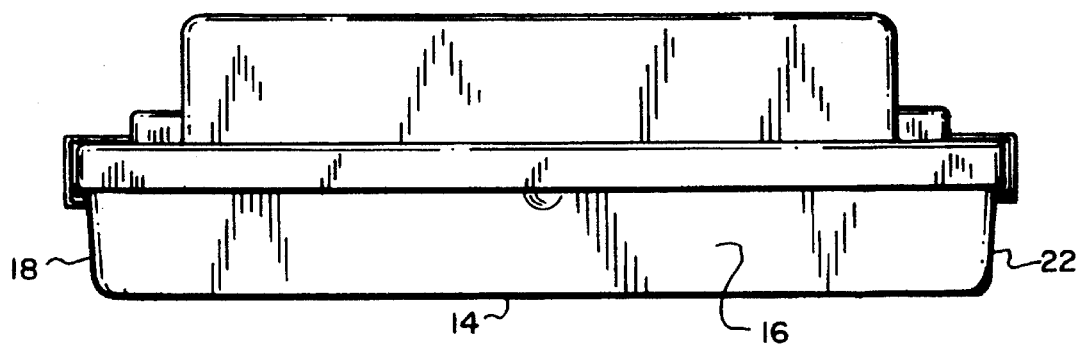
FIG. 2 is a side elevational sectional view of tray assembly of FIG. 1.
Figure 3:
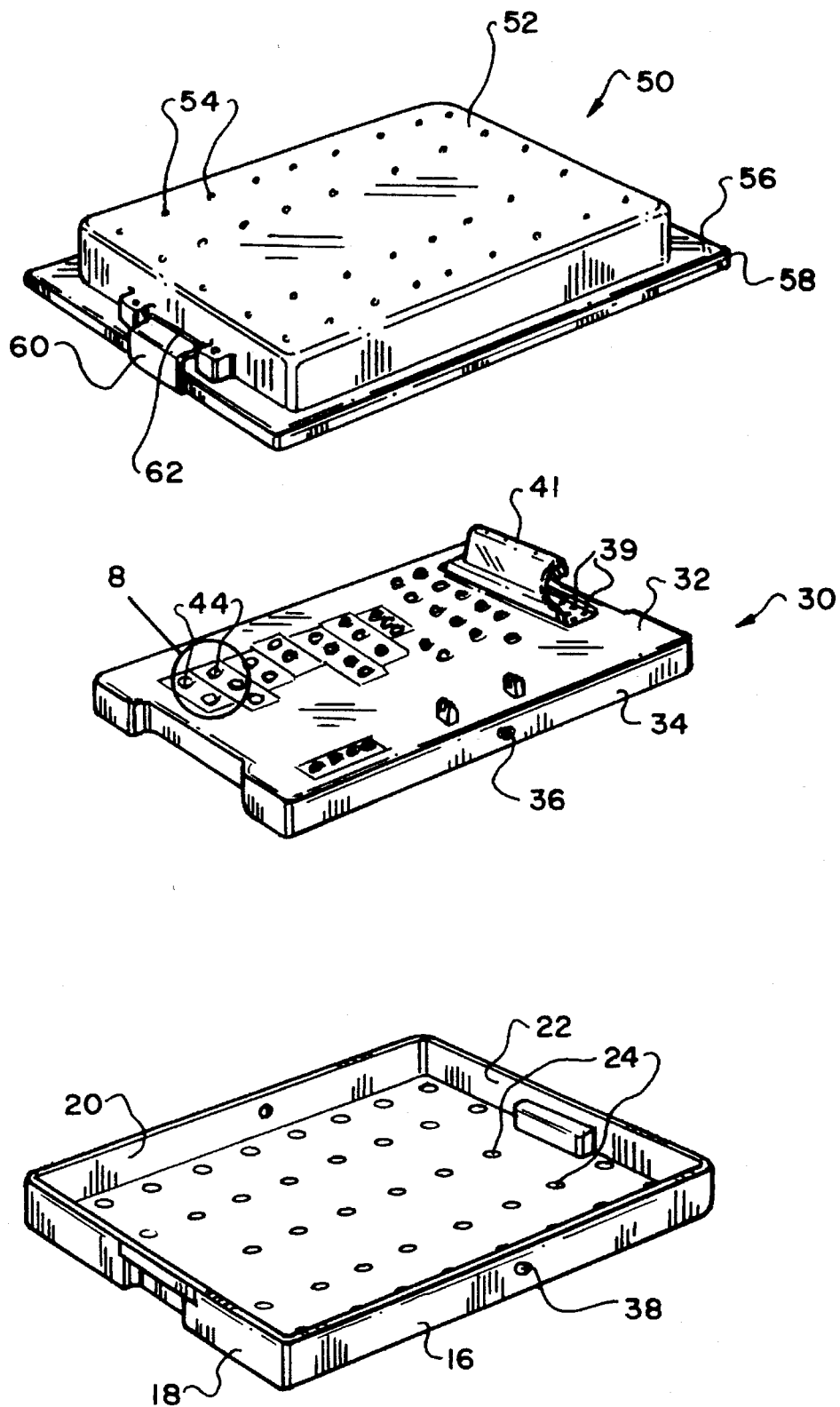
FIG. 3 is a partially exploded view of FIG. 1.
Figure 4:
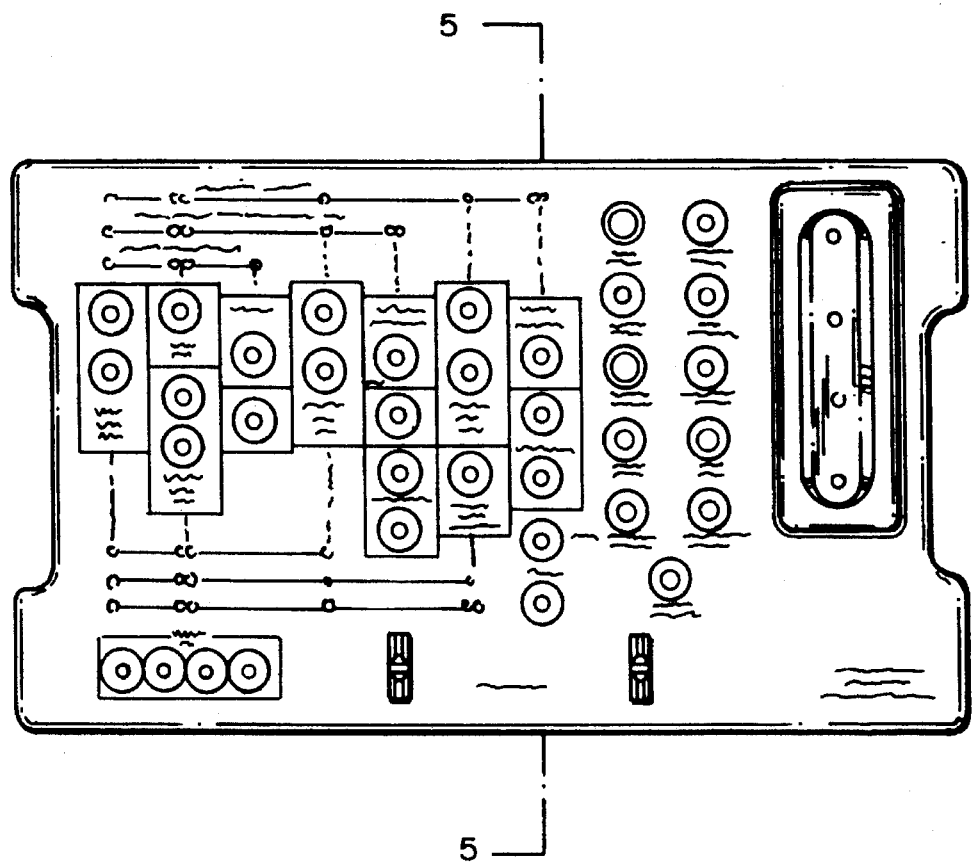
FIG. 4 is an overhead plan view of the tray assembly of FIG. 3, with the top tray removed.

Completing the sterilization and storage container tray of the present invention are C-shaped locking hinges 60 made of a flexible metal or plastic which are attached to top 50 by hinge pins 62 at the midpoint position of the opposite ends of top 50 as shown in FIGS. 1–3. As seen in particular in FIG. 6, the locking hinges 60 pivot about hinge pins 62 between a locking and non-locking position (shown in phantom in FIG. 6).

Figure 6:
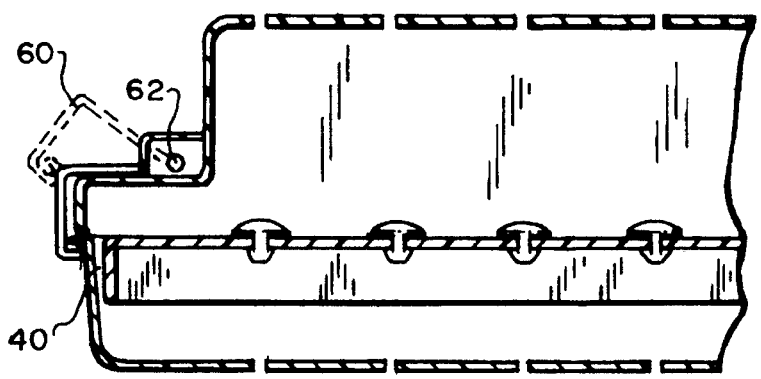
FIG. 6 is a partial sectional view taken along line 6—6 of FIG. 1.

Alternatively, and particularly in the case of larger sterilization, transporting and storage container trays, locking hinges also may be mounted both at midway positions at opposite ends of the top 50 and also at midway positions of opposite sides of the top. The additional pair locking hinges may comprise generally C-shaped spring hinges as shown in FIG. 6, but in a preferred embodiment of the invention at least one pair of the locking hinges comprises generally C-shaped clamps 70, pivotally mounted by pins 72 to a camming handle 74 which is in turn attached to cover 50 by pins 76. (See FIGS. 7A and 7B.) Also, if desired, lifting handles 80 may be provided to facilitate handling of the tray assembly.

Figure 7A:
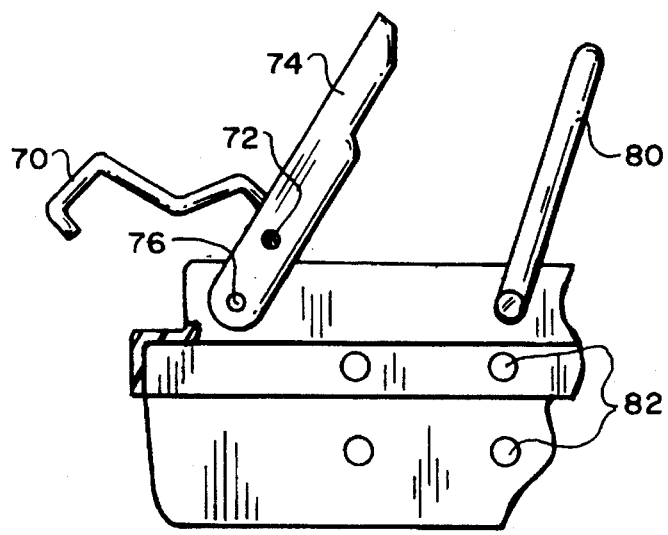
FIGS. 7A and 7B are partial sectional views showing an alternative locking mechanism in accordance with the present invention.
Figure 7B:
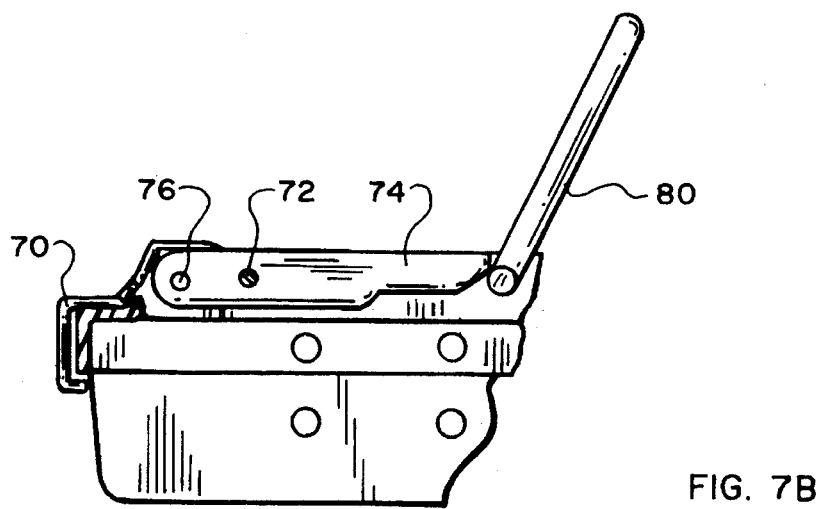

While particular embodiments of the present invention have been illustrated and described herein, it is not intended to limit the invention, and changes and modifications may be made therein without departing from the scope of the invention. For example, additional spaced apertures 80 may be arranged in the side walls of base 12 and top 50 to provide additional locations for ingress of steam and other gaseous sterilants during sterilization. Also, if desired, a plurality of apertures 82 may be provided in the sidewalls of the tray assembly 30 for permitting additional flow of steam or other gaseous sterilants during sterilization, and drainage of condensation from the top surface of the tray. Additionally, the tray assembly may comprise only cammed locking clamps 70 as shown in FIGS. 7A and 7B.

While particular embodiments of the present invention have been illustrated and described herein, it is not intended to limit the invention and changes and modifications may be made thereon within the scope of the following claims.

What is claimed is:

1. A sterilization tray assembly for sterilizing, transporting and storing surgical instruments, comprising top and bottom mating enclosures, said mating enclosures each comprising a plurality of ports for permitting ingress and egress of gaseous sterilant; a rack dimensioned to fit within the bottom enclosure, said rack having a plurality of spaced apertures into which are mounted grommets formed of an elastomeric material having an inside diameter dimensioned to receive a selected surgical instrument therein; and means for locking said mating enclosures to one another.

2. In a tray assembly according to claim 1, wherein said grommets each include a plurality of inwardly directed ribs for gripping a surgical instrument therein.

3. In a tray assembly according to claim 1, wherein the apertures in said rack are all of equal size, and said grommets have inside diameters of varying sizes to accommodate selected instruments therein.

4. In a tray assembly according to claim 1, and including indicia keyed to surgical instruments printed on the rack.

5. In a tray assembly according to claim 1, and including indicia keyed to surgical instruments printed on the top enclosure.

6. In a tray assembly according to claim 1, and including an apertured riser carried by the tray within the assembly for enhancing distribution of gaseous sterilant.

\* \* \* \* \*